United States Patent [19]
Grudzien, Jr. et al.

[11] Patent Number: 5,308,953
[45] Date of Patent: May 3, 1994

[54] HEATER BLOCK HOLDER FOR A CAPILLARY RHEOMETER PLUNGER PRESSURE TRANSDUCER

[75] Inventors: Christopher P. Grudzien, Jr., Mansfield, Mass.; Robert Malloy, Londonderry, N.H.

[73] Assignee: Dynisco, Inc., Sharon, Mass.

[21] Appl. No.: 970,309

[22] Filed: Nov. 2, 1992

Related U.S. Application Data

[62] Division of Ser. No. 680,561, Apr. 4, 1991, Pat. No. 5,209,107.

[51] Int. Cl.⁵ .................. G01N 11/08; H05B 1/00
[52] U.S. Cl. .................... 219/242; 73/54.43; 219/385; 219/521
[58] Field of Search ............... 73/54.01, 54.02, 54.11, 73/54.43, 54.42; 219/242, 521, 535, 385, 386

[56] References Cited

U.S. PATENT DOCUMENTS

| | | | |
|---|---|---|---|
| 1,061,289 | 5/1913 | Heyder | 219/242 X |
| 1,824,585 | 9/1931 | Wolcott et al. | 219/521 |
| 2,299,401 | 10/1942 | Melton | 219/521 X |
| 2,487,161 | 11/1949 | Melton | 219/521 |
| 2,562,821 | 7/1951 | Rothweiler | 219/242 X |
| 2,907,861 | 10/1959 | Melton | 219/242 X |
| 3,983,363 | 9/1976 | Alter | 219/242 X |

FOREIGN PATENT DOCUMENTS

| | | | |
|---|---|---|---|
| 208943 | 11/1955 | Australia | 219/242 |
| 1051578 | 12/1966 | United Kingdom | 219/242 |

*Primary Examiner*—Anthony Bartis
*Attorney, Agent, or Firm*—Wolf, Greenfield & Sacks

[57] ABSTRACT

A capillary rheometer plunger having a liquid-filled capillary passage extending within the plunger is removably housed in a heater block holder for maintaining temperature stability and minimizing temperature induced errors. The plunger is placed in the holder during purging, cleaning, reloading and packing the capillary rheometer with the polymer under test. The holder includes an electrically heated holder member disposed within an aperture of an outer shield and is provided with an aperture in which the plunger is removably received for heating. A base supports the shell. A temperature sensor disposed in the shell controls the temperature of the holder member at the temperature of the polymer under test.

3 Claims, 8 Drawing Sheets

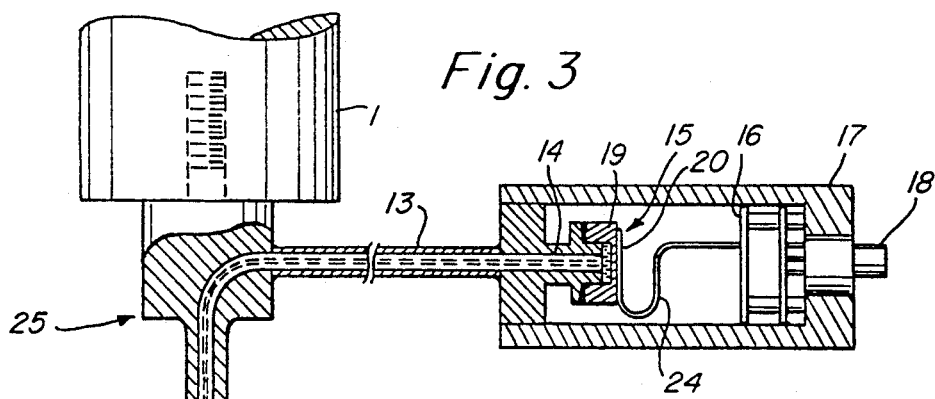
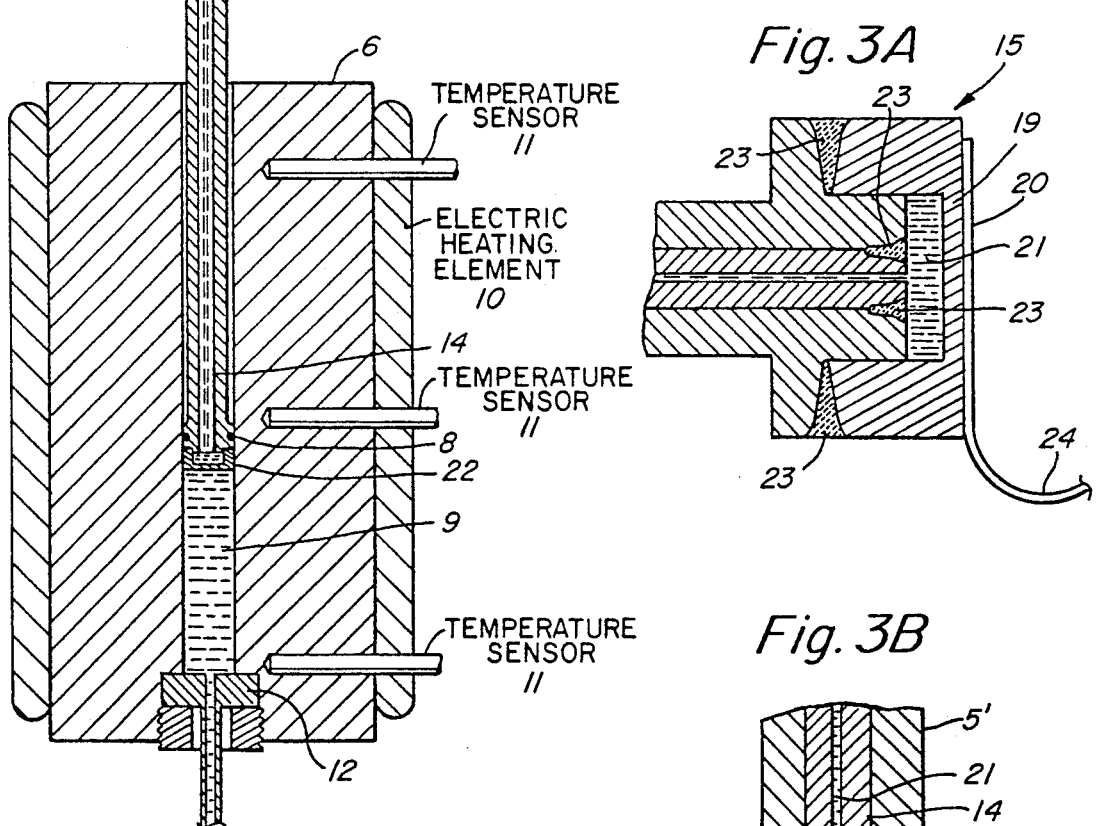
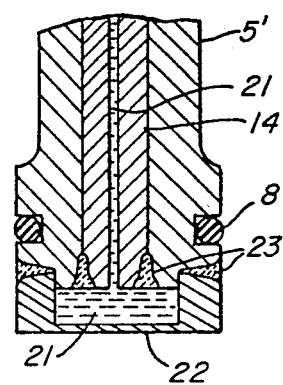

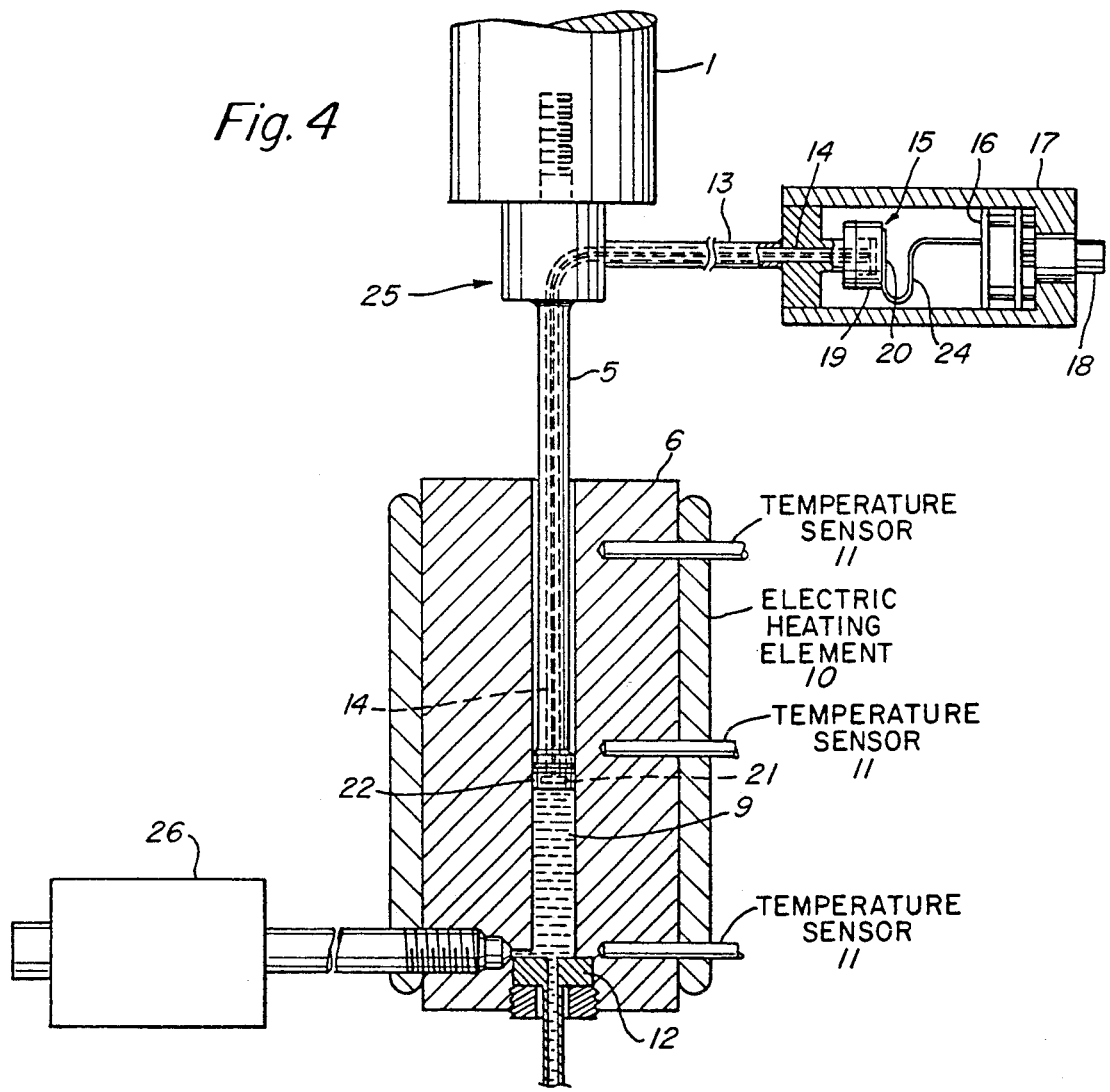

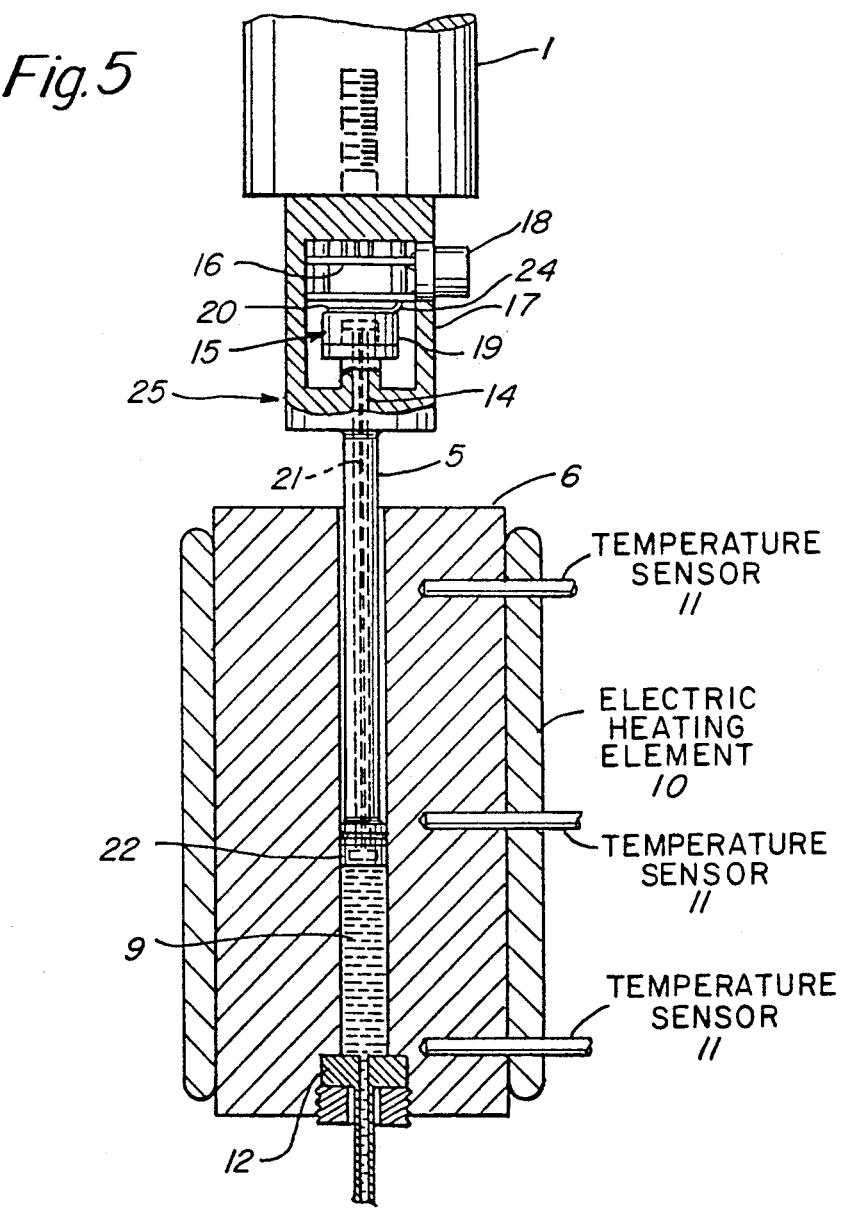

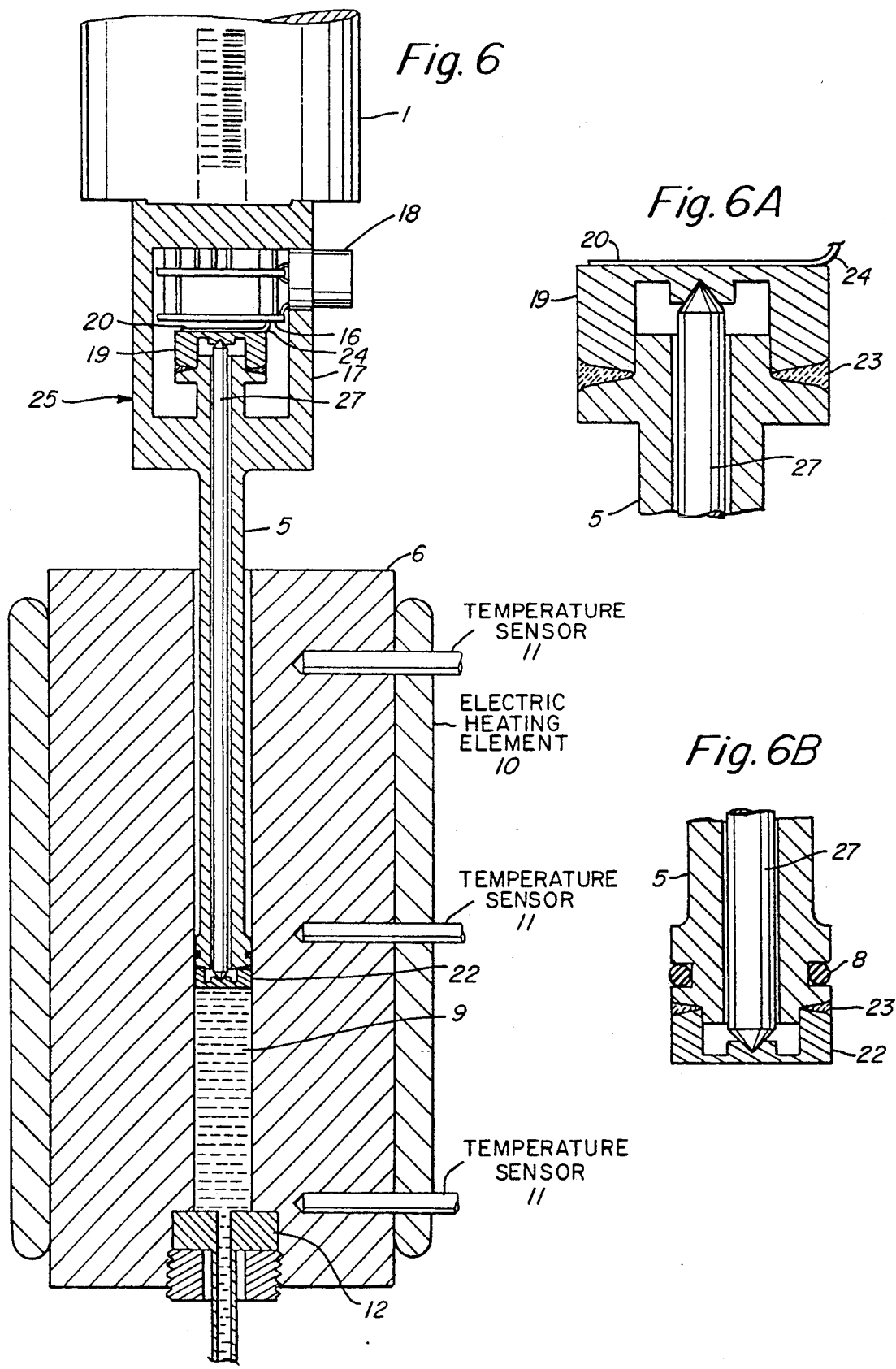

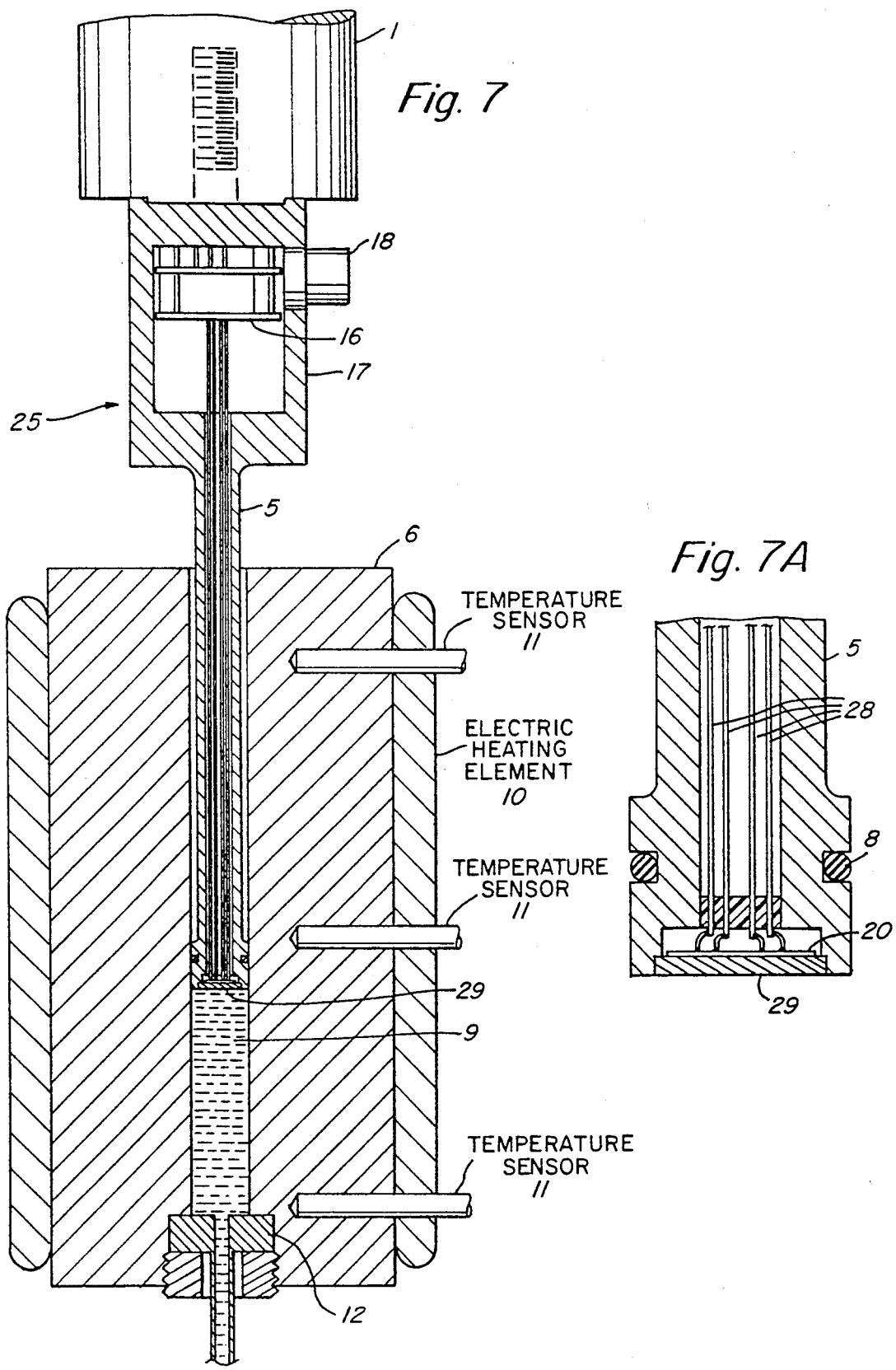

HEATER BLOCK HOLDER FOR A CAPILLARY RHEOMETER PLUNGER PRESSURE TRANSDUCER

This application is a division of application Ser. No. 07/680,561 filed on Apr. 4, 1991, now U.S. Pat. No. 5,209,107, granted May 11, 1993.

BACKGROUND OF THE INVENTION

1. Field of the Invention

The present invention relates to a capillary rheometer for establishing shear and temperature related material properties and pertains, more particularly to a capillary rheometer which utilizes a pressure measurement plunger for such purposes.

2. Background

Various types of capillary rheometers are utilized in the polymer industry to establish shear and temperature related material properties. The theory of operation and design specifications for capillary rheometers are documented in U.S. Pat. No. 3,203,225.

Capillary rheometers generally operate by using a piston or plunger to force melted polymers, that have been heated in a barrel passage, through a capillary die. The force based plunger-barrel capillary rheometer utilizes a force sensor to measure the load or force applied to the plunger and a displacement sensor to measure a given plunger velocity (displacement/unit time) through the stationary barrel. The apparent shear viscosity of the melted polymer can be determined using known relationships for flow of polymer melts through the cylindrical or other commonly used geometries. For example, wide through or annulus geometries may be used. The apparent shear viscosity of a polymer melt at a given melt temperature is determined using the ratio of wall shear stress divided by apparent wall shear rate, for the capillary of a defined geometry. The wall shear stress depends upon the plunger force measured by the force sensor. There are, however, a number of errors associated with the melted polymer apparent viscosity data determined using the above mentioned method because both the shear stress and the apparent shear rate values have errors associated therewith. Particularly, the plunger force (in which the volume flow rate is determined from the plunger displacement stroke, which is usually very small) measured by the force sensor is inaccurate. These errors will be described, in particular, with reference to a prior art embodiment of the present invention, as illustrated in FIGS. 1 and 2.

Shear stress values will be in error if determined by means of a force sensor, because the force at the top of the plunger is influenced by the following factors which are not considered when the force sensor method is employed:

1. The Pressure Drop in the Barrel: The barrel 6 of the capillary rheometer is itself a capillary of given diameter and continuously decreasing effective length as the plunger 5 moves downward. The force required to maintain flow through the barrel 6 (i.e., pressure drop along barrel 6) is significant, especially since the shear rate associated with barrel flow is low, and melted polymers have relatively high viscosities at low shear rates as most polymers are pseudoplastic in nature. The pressure drop is not considered by the force sensor measurement and thus a resulting error occurs. In addition, this error is not a "constant" at a given temperature and plunger 5 speed since the effective length of the barrel 6 changes continuously.

2. Friction Between Plunger and Reservoir Wall: In order to minimize the flow of material back across the land of the plunger 5, the plunger 5 must be fitted tightly within the barrel 6. The plunger 5 may be relieved some distance back form the melted polymer 9 interface, although enough tightly fitted land must remain to (i) limit the back flow of melted polymer 9 and (ii) align the base of the plunger 5 in the barrel 6. Low coefficient of friction plunger seals 8 are often used to reduce the back flow of the melted polymer 9.

The melted polymer 9 may stick to the wall of the barrel and may be sheared between the wall and the plunger 5 as the plunger 5 moves. The plunger 5 itself will rub against the barrel 6 wall unless it is perfectly straight, properly aligned, and has the correct dimensions. High pressures in the barrel 6, such as those encountered when working with viscous materials at high flow rates, could cause buckling of the plunger 5 within the barrel 6, and binding between the plunger 5 and barrel 6. The dimensions of both the plunger 5 tip and barrel 6 will also change when the operating temperature is changed. Changes in operating temperatures could result in scoring of the barrel 6, or the opening of the gap through which back flow can occur. Therefore, plunger friction errors are likely to occur.

Plunger 5 friction errors are typically estimated by removing the capillary 12 and measuring the force required to. force melted polymer 9 from the barrel 6, and extrapolating this to force data to a zero barrel length. The method has been criticized since the friction errors vary with driving pressure and flow rate, and it is also time consuming.

3. End Errors: The entrance area of capillary 12 and barrel 6 exit area is a region where large stresses are developed due to the funneling of the melted polymer 9 as it emerges from the barrel reservoir, as well as region where these stresses relax to their limiting value which occurs some distance along the length of the capillary 12 tube.

The exit pressure for capillary 12 has also been shown to be somewhat greater than zero for viscoelastic polymers. The exit pressure is the result of recoverable elastic energy within the melted polymer 9, caused by flow induced orientation of the polymer molecules during deformation upstream of the capillary 12 exit. Purely viscous materials have exit pressures of zero.

The end errors can be minimized using dies having longer L/D ratios, and reducing the relative magnitude of the errors, since they are essentially constants at a given temperature and rate, being independent of capillary 12 length. It should be appreciated that the end errors are a constant and, therefore, become smaller on a percentage basis as the capillary length increases. The errors can be eliminated using the procedure of classical hydrodynamics of plotting the pressure drop measured over a system containing both an entrance region and straight capillary 12 versus the L/R of the tube, for tubes of various lengths and constant diameter at each flow (or shear) rate. Extrapolation to a pressure drop of zero gives the end effect in terms of absolute pressure or tube radii. An alternative method is to use a flow geometry, such as a wide thin slit, for which the pressure drop within the rheometric region of the flow can be measured directly.

4. Temperature and Compressibility: It is generally assumed that the temperature of the melted polymer 9 is constant, and that the melted polymer 9 is incompressible. Melted polymers 9 are in fact, however, compressible, and are generally viscous materials, having relatively low thermal diffusitivities, indicating that the temperature of the polymer is likely to increase as it progresses through the measurement system due to viscous dissipation, to a degree depending on conductive heat loss. In order to minimize viscous heating and compressibility effects, short L/D capillaries 12 are recommended, provided end errors and barrel 6 related errors can be accounted for, since their relative effect is more significant for shorter capillaries 12.

The force/pressure calculation does not take into consideration the clearance area between the plunger 5 and the barrel 6 wall.

5. Elastic distortion: Elastic distortion of the barrel and polymer viscosity both change with temperature and pressure, plunger velocity, alignment and force. These changes as well as seal quality affect the calculation of effective area used to determine the pressure generated within the barrel of the capillary rheometer. The exact magnitude of these errors in a capillary rheometer are unknown although elastic distortion and effective area calculations are well documented for dead weight piston gages.

The force/sensor pressure calculation does not take into consideration the clearance area between the plunger and the inner barrel wall. The elastic distortion of the barrel and polymer viscosity change with temperature and pressure and plunger velocity. These unaccounted for changes cause errors in effective area and other related calculations.

6. Polymer Backflow/Leakage/Shear Rate Errors: The rate at which melted polymer 9 flows through the capillary 12 is assumed to be equivalent to the value determined using the distance swept by the plunger 5 per unit time, assuming incompressibility and mass conservation. There will however be some leakage of material across the land of the plunger 5, since the pressure on the melted polymer 9 is greater than atmospheric. The amount of back flow will be determined by the quality of the plunger seal 8. Close, tight tolerances between the barrel 6 and plunger 5 will reduce leakage. An increase in the land length (contact area) will also reduce leakage. However, an increase in the number of plunger seals 8, or in the contact area between the plunger 5 and barrel 6, is also expected to increase the magnitude of the plunger 5 barrel 6 friction force errors.

Force sensor pressure calculations do not take into consideration some leakage of the melted polymer across the plunger. There is, however, some leakage of the melted polymer across the plunger. Thus, errors are associated with this calculation. By increasing the number of plunger seals or the contact area between the plunger and inner barrel wall, while it reduces the leakage, it increases the friction errors.

Accordingly, it is an object of the present invention to provide an improved capillary rheometer which eliminates the need for a force based measurement plunger.

It is another object of the present invention to provide a capillary rheometer in which accurate shear stress and apparent shear rate values for a melted polymer can be determined.

It is another object of the present invention to provide a capillary rheometer which will eliminate the need for corrective methods to account for errors due to the barrel pressure drop, friction between the plunger and inner barrel wall, and errors, temperature and compressibility errors, elastic distortion errors, leakage errors and other related errors.

It is another object of the present invention to provide a capillary rheometer which utilizes a pressure measurement plunger.

It is another object of the present invention to provide a capillary rheometer which utilizes a pressure sensor for sensing pressure exerted by the melted polymer.

A heater block holder system is disclosed for housing a capillary rheometer plunger and includes: an outer shell having a first aperture defined therein, a holder member disposed within the first aperture, the holder member having a second aperture defined therein for housing a capillary rheometer plunger, the capillary rheometer plunger includes, in a preferred embodiment, a liquid-filled capillary passage extending within the plunger, and a base for supporting the block.

BRIEF DESCRIPTION OF THE DRAWING

Numerous other objects, features and advantages of the invention should now become apparent upon a reading of the following detail description taken in conjunction with the accompanying drawings, in which:

FIG. 3 is a cross-sectional view of the capillary rheometer of the present invention, illustrating use of the plunger pressure transducer assembly;

FIG. 3A is an exploded fragmentary view of the sensing diaphragm;

FIG. 3B is an exploded fragmentary view of the tip diaphragm;

FIG. 4 is a cross-sectional view of an alternate embodiment of the present invention illustrating the use of an additional pressure style transducer;

FIG. 5 is a cross-sectional view of an alternate embodiment of the present invention illustrating a liquid metal filled, rigid stem, capillary rheometer plunger transducer;

FIG. 6 is a cross-sectional view of an alternate embodiment of the present invention illustrating a push rod, rigid stem, capillary rheometer plunger transducer;

FIG. 6A is an enlarged, fragmentary, cross-sectional view of the push rod, rigid stem, plunger transducer of the capillary rheometer of FIG. 6;

FIG. 6B is an enlarged, fragmentary, cross-sectional view of the push rod, rigid stem, plunger transducer of the capillary rheometer of FIG. 6;

FIG. 7 is a cross-sectional view of an alternate embodiment of the present invention illustrating a non-bonded piezo resistive type, rigid stem, capillary rheometer plunger transducer;

FIG. 7A is an enlarged, fragmentary, cross-sectional view of the non-bonded piezo resistive plunger transducer of the capillary rheometer of FIG. 7;

DETAILED DESCRIPTION OF THE PREFERRED EMBODIMENT

In accordance with the present invention there is provided a capillary rheometer which utilizes a plunger pressure transducer assembly. This plunger pressure transducer assembly has a plunger with one end for forcing a melted polymer through a capillary and a diaphragm at the end of the plunger sensing pressure in the polymer. It additionally has a capillary passage with a liquid metal fill fluid therein as well as another sensing diaphragm, located at the opposite end of the pressure transducer assembly from the plunger. As the plunger is lowered and pressed on to the top of the melted polymer, generating a pressure internal to the melted polymer, the diaphragm at the tip of the plunger, nearest the melted polymer, senses the melted polymer pressure, and transmits this pressure to the liquid metal fill fluid in the plunger pressure transducer assembly. Then the other sensing diaphragm at the opposite end of the plunger pressure transducer assembly senses the pressure within the liquid metal fill fluid and yields an accurate pressure measurement immune to any of the friction or pressure drop related errors common to force based plunger measurement techniques.

Figure 1:
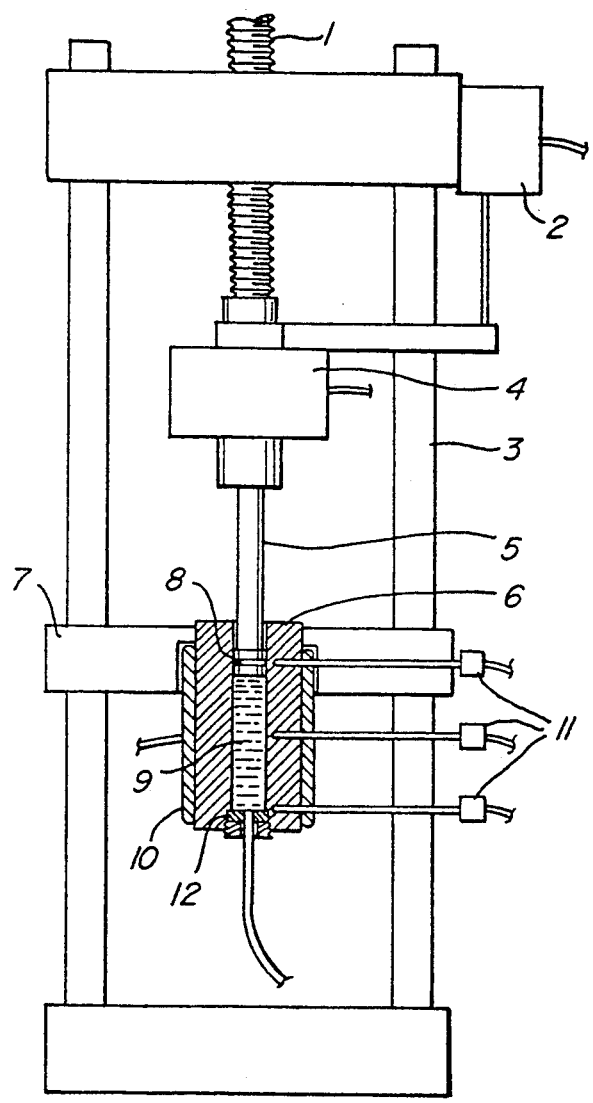
FIG. 1 is an elevational partially broken view of a prior art embodiment of a force based capillary rheometer including a force sensor.
Figure 2:
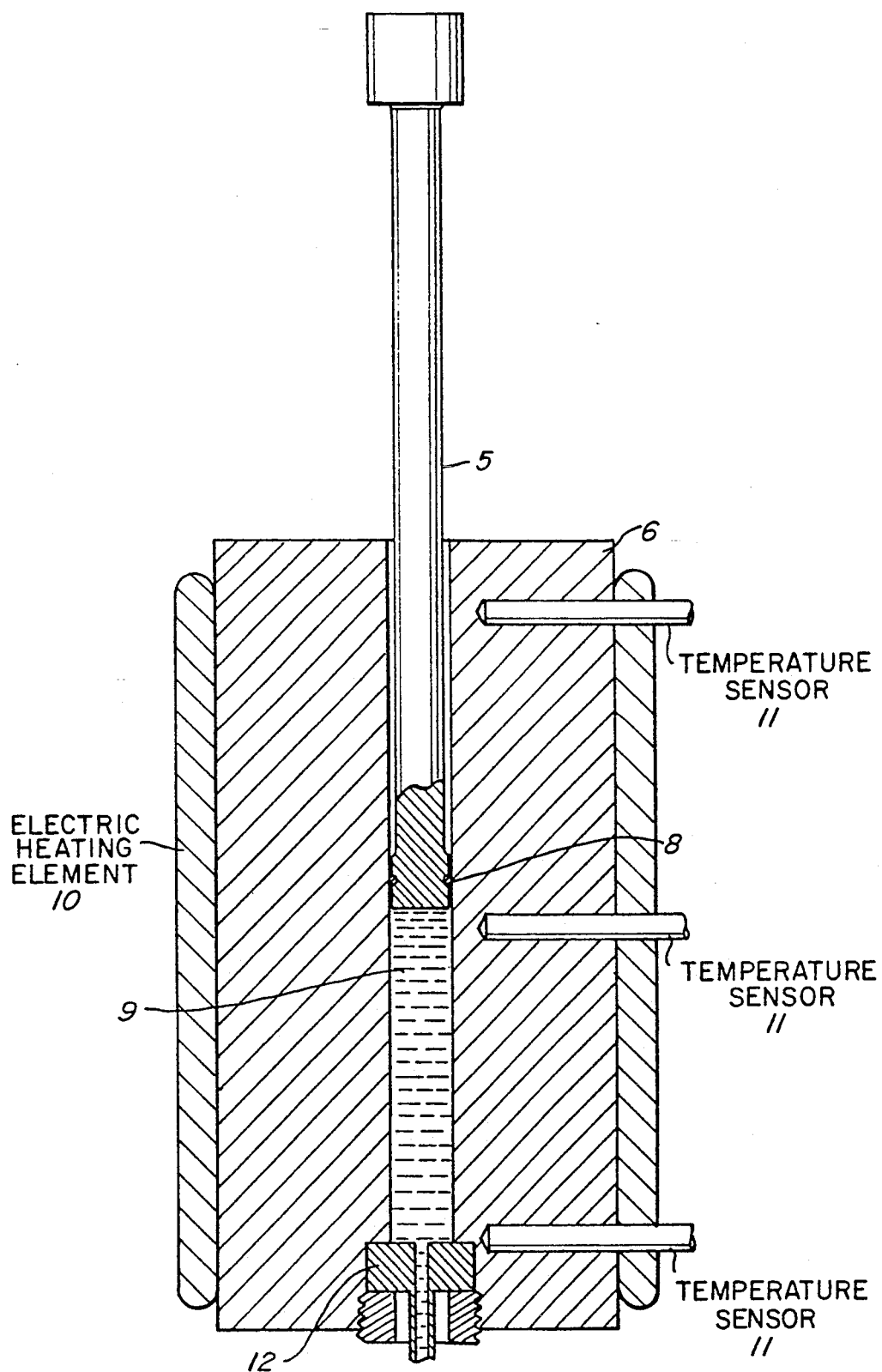
FIG. 2 is an enlarged cross-sectional view of the prior art force based capillary rheometer, illustrating in particular the force based plunger and the entrance to the capillary.

Reference is now made to the drawings and, in particular, to FIGS. 1 and 2 in which a prior art embodiment of the force based capillary rheometer is illustrated. A preferred embodiment of the present invention, illustrating the capillary rheometer with the pressure plunger transducer is shown FIG. 3. Alternate embodiments of the present invention, utilizing the plunger pressure transducer, are illustrated in FIGS. 4–8.

Referring now in particular to FIGS. 1 and 2, which illustrate a standard force based type capillary rheometer, the force sensor 4 can be seen for measuring force of the plunger 5. Due to the aforementioned errors associated with this method, the present invention utilizes a pressure transducer assembly 25, replacing the force based measurement plunger, as illustrated in FIG. 3.

Force base plunger type capillary rheometers, as illustrated in FIGS. 1 and 2, use a piston or plunger 5 to force melted polymers, that have been heated in-situ, through a capillary die 12. The force, or melt pressure (calculated using the force measured by the force sensor 4 divided by the effective area of the plunger 5 required to maintain steady flow through the capillary die 12 at a given plunger velocity) is measured, and is indicative of the polymers apparent shear viscosity.

The force based plunger-barrel capillary rheometer utilizes a force sensor 4 to measure the load applied to the plunger 5 in order to maintain a given plunger 5 velocity through the stationary barrel 6. The apparent shear viscosity of the melted polymer 9 can be determined using the relationships for flow of polymer melts through cylindrical geometrics (i.e. pipe pressure flow). The apparent shear viscosity of the polymer melt at a given melt temperature and pressure, at the wall of the capillary 12, is determined by the ratio of wall shear stress divided by apparent wall shear rate, for the capillary 12 of defined geometry. The pressure gradient along the length of the capillary 12 is indicative of the shear stress. The capillary 12 entrance pressure at each temperature and shear rate is calculated using the plunger 5 force measured by the force sensor 4 divided by the effective area of the plunger 5. The discharge pressure of the capillary 12 is assumed to be zero, so the pressure gradient is the capillary 12 entrance pressure divided by the capillary 12 length. The apparent shear rate at the wall of the capillary 12 is calculated from the melted polymer 9 flow rate through the capillary 12, which is determined by monitoring the position of the piston by means of a displacement sensor 2 in the barrel with respect to time assuming melted polymer 9 incompressibility and mass balance.

Also illustrated in FIGS. 1 and 2 is the load screw 1 which can be driven by electromechanical or servohydraulic/electromechanical, servohydraulic-pneumatic means, or using weights and the force of gravity. The problem with using weights, however, is that perfect alignment is necessary, which in turn causes a lot of friction. In addition, the support columns 3 are shown for supporting the plunger 5 and barrel 6. In addition, a support bracket 7 is shown supporting the barrel 6 between the support columns 3. Also shown are the plunger seals 8 for containing the melted polymer 9 within the barrel 6. In addition, the heater 10 is shown for heating of the barrel 6, as well as temperature sensors 11 for temperature detection thereof.

The aforementioned errors associated with these force based capillary rheometers, however, render them inaccurate.

The present invention provides a capillary rheometer in which the aforementioned errors and corrective techniques are avoided. FIG. 3 illustrates a preferred embodiment of the capillary rheometer of the present invention in which a pressure transducer assembly plunger replaces the old force based measurement plunger. The capillary rheometer, as shown in FIG. 3, consists of a barrel 6 heated by an electrical power-controlled heater 10 with an appropriate capillary 12 retained at the bottom. The plunger 5 (as shown in FIG. 2) has been replaced by a plunger pressure transducer assembly 25. The plunger pressure transducer assembly 25 is moved downward by the motor, a dead weight, or a pneumatic, mechanical, or hydraulically driven drive head, in a controlled rate of descent or at a constant stress. It is to be appreciated that pneumatic rheometers typically employ a constant pressure rather than a constant speed as in the motorized type. The diaphragm 22 of the plunger pressure transducer assembly 25 presses onto the top of the melted polymer 9 generating a pressure internal to the melted polymer 9 and the liquid metal fill fluid 21, as will be described below. The plunger seal 8 prevents the melted polymer 9 from escaping around and past the plunger pressure transducer assembly 25 and out the top of the barrel 6 and the associated seal friction is not considered in the pressure measurement. Melted polymer 9 begins to flow through the capillary 12 in a calculable manner. The tip diaphragm 22 transmits the melted polymer pressure, in this configuration, to a fill liquid metal fluid 21 within the metal capillary 14 in the plunger pressure transducer assembly 25. The sensing diaphragm 19 deflects in response to the transmitted pressure of the liquid metal fluid 21, straining the four strain sensitive resistive elements within strain gage 20. The four strain sensitive resistive gage elements are arranged in a Wheatstone bridge configuration, with two increasing and two decreasing resistive elements. The strain induced resistive changes are then transformed into a voltage change. The voltage change is directly proportional to the pressure change in the Capillary Rheometer barrel 6 and inversely proportional to the voltage supplied to the Wheatstone bridge. Further details of the sensing diaphragm are illustrated in the exploded fragmentary of FIG. 3A. Similarly, further details of the tip diaphragm 22 are illustrated in the exploded fragmentary view of FIG. 3B.

In accordance with this preferred embodiment of the present invention, as illustrated in FIG. 3, further details of the plunger transducer assembly 25 will be described below. The metal capillary 14 can be seen within the metal armor flex hose 13 for flexible movement. The metal capillary 14 encloses the liquid metal fill fluid 21. Tube 14 is welded at 23 to plunger 5 and metal case 17 at its ends. Tube 14 is then filled and capped off with diaphragms 22 and welds 23. The measurement diaphragm assembly 15 acts to measure the pressure of the liquid metal fill fluid 21 within the metal capillary 14. The measurement diaphragm assembly 15 includes the temperature compensation printed circuit board assembly 16. Strand gage 20 is attached to circuit board 16 via flexible circuit board 24. This measurement diaphragm assembly 15 is enclosed in metal case 17. An electrical connector 18 is provided on the periphery of the metal case 17.

Figure 8:
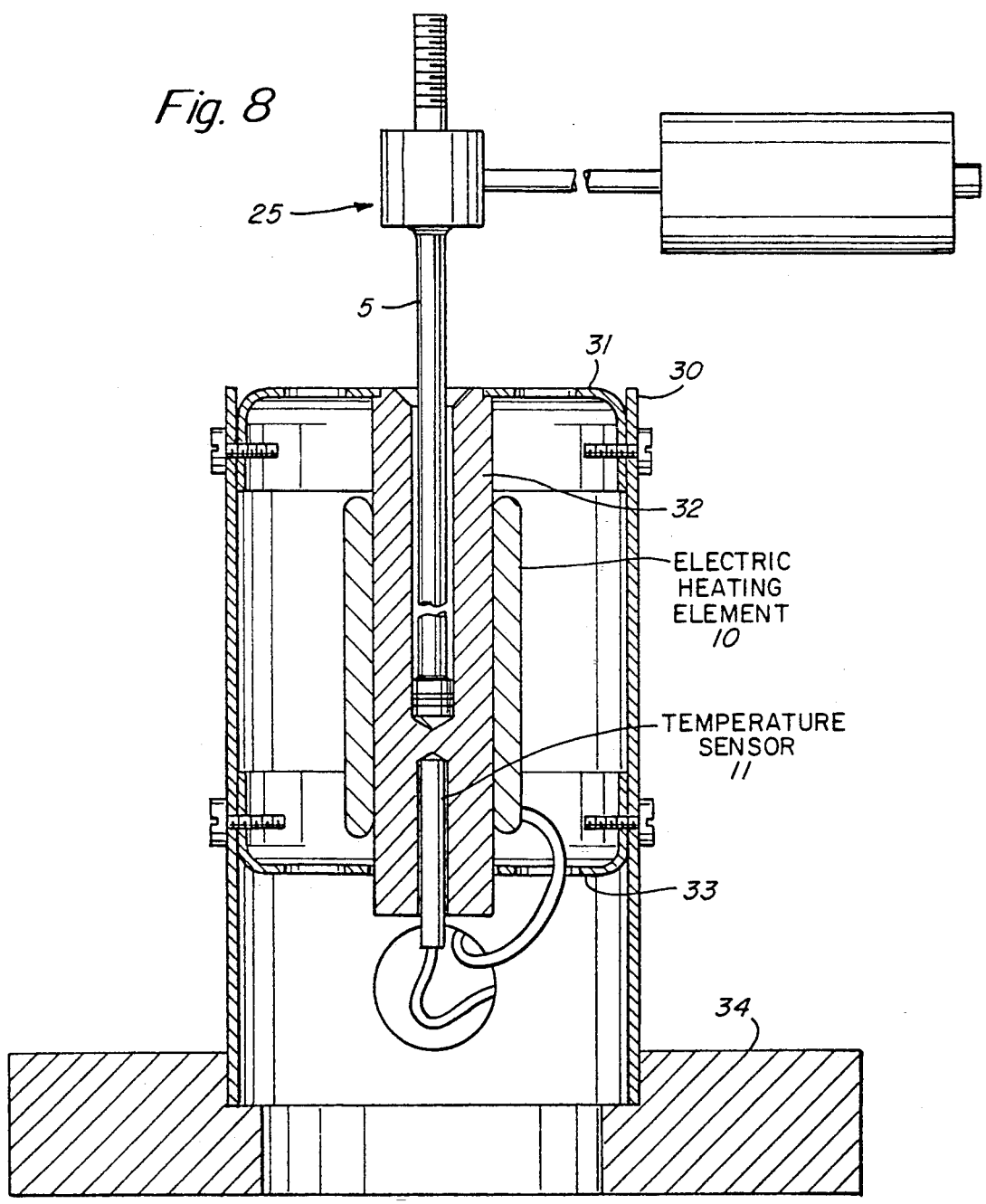
FIG. 8 is a cross-sectional view of an alternate embodiment of the present invention illustrating use of a heater block holder for the capillary rheometer plunger transducer.

In an alternate embodiment of the present invention, in order to maintain thermal stability and minimize temperature induced errors in the plunger transducer assembly 25 during operation with the capillary rheometer, a heater block holder is utilized, as illustrated in FIG. 8. The capillary rheometer plunger transducer rests within a holder 32, which is heated by an electrical heater 10 to the temperature of the polymer under test, measured by the temperature sensor 11 and controlled by a conventional temperature controller (not shown). The base 34 supports the outer cylindrical shell 30, which acts as a heat shield for the holder 32 and the heater 10. The upper 31 and lower 33 plates support and maintain centrality, respectively, of the holder 32 and provide a plenum for air circulation from the holes provided in the outer cylindrical shell 30 through to the lower 33 and upper 31 plates.

The plunger pressure transducer assembly 25 is placed in the holder 32 during purging, cleaning, reloading and packing of the polymer under test in the capillary rheometer. The plunger pressure transducer assembly 25 is removed from the holder 32, inserted into the capillary rheometer barrel 6 and allowed to thermally stabilize for a short period of time prior to testing. With the plunger pressure transducer assembly 25, pressure measurements are made as opposed to force based plungers with which force measurements are made. Thus, the implementation of a plunger transducer assembly 25 into a forced based type capillary rheometer, eliminates errors related to the seal frictional force component. In addition, the implementation of a plunger transducer assembly 25 into a forced based capillary rheometer eliminates the clearance area uncertainties from the pressure measurement calculations required to establish a polymeric material's shear viscosity. Better sealing can be achieved and therefore lower shear rate uncertainty achieved, since the improved sealed quality can be used with no influence on the measured pressure value.

The viscosity of the polymer in the barrel 6 of the capillary rheometer can be determined using the plunger transducer assembly 25 (i.e., the viscosity of the polymer at shear rates lower than those encountered in the primary capillary) if the difference between the plunger 5 and barrel 6 discharge pressure can be measured.

The addition of another melt pressure style transducer 26, as shown in FIG. 4 with a rheometer which utilizes a pressure transducer before the capillary dye would allow the measurement of the pressure difference. It should be appreciated, however, that the use of the combination plunger/pressure transducer in conjunction with a rheometer which utilizes a pressure transducer before the capillary dye does not offer the advantages that it does when implemented in a standard force based capillary rheometer, since the barrel pressure drop or plunger friction errors are not encountered with this rheometer. The use of such a device, however, with the with a rheometer which utilizes a pressure transducer before the capillary dye would allow one to evaluate viscosity at low barrel and high capillary shear rates at each plunger speed since the barrel itself can be considered a large diameter capillary.

Barrel reservoir pressure drop (or head effect) is one of the factors that contributes to the force reading for piston rheometers which utilize compressive load sensors at the upper end of the piston. The barrel pressure drop error is described as being significant. The existence of this error has in fact influenced certain rheological measurement practices.

Extrusion plastometer (melt flow rate) measurements must be made within certain piston height limits.

Development of piston rheometers which utilize pressure transducers at the entrance to the capillary die eliminate the pressure drop error because measurements are downstream from the barrel.

The barrel pressure drop is equivalent to:

$$\Delta P_B = \frac{8 Q_B \eta_B L_B}{\pi (R_B)^4}$$

where:
$Q_B$ = volume flow rate through the barrel
$\eta_B$ = viscosity of the material in the barrel
$R_B$ = radius of the barrel (inner)
$L_B$ = effective length of the barrel (the distance between the piston top and capillary end.)
while the capillary pressure drop is equivalent to:

$$\Delta P = \frac{8 Q_C \eta_C L_C}{\pi (R_C)^4}$$

where:
$Q_C$ = volume flow rate through the capillary
$\eta_C$ = viscosity of the material in the capillary
$L_C$ = length of the capillary
$R_C$ = radius of the capillary For a Newtonian, uncompressible fluid, the ratio of the barrel pressure drop to the capillary pressure drop (which is an indicator of the magnitude of the error) is equivalent to:

$$\frac{\Delta P_B}{\Delta P_C} = \left| \frac{R_C}{R_B} \right|^4 \times \left| \frac{L_B}{L_C} \right|$$

The error decreases as the test progresses because the effective length of the barrel decreases continuously throughout the test.

Most plastic materials are pseudoplastic in nature, having viscosities that decrease with increasing shear rate. For non-Newtonian materials, such as plastic melts, this ratio is:

$$\frac{\Delta P_B}{\Delta P_C} = \frac{q_B L_B (R_C)^4}{q_C L_C (R_B)^4}$$

where $q_B > q_C$ and for highly pseudoplastic polymers, $q_B >> q_C$, since the shear rates in the larger diameter barrel are much lower than those in the typically smaller diameter capillary at the same volume flow rate. The barrel pressure drop error is, therefore, more significant for pseudoplastic materials (for a given rheometer and capillary geometry).

The alternate embodiment capillary rheometer, as shown in FIG. 4, utilizes two pressure transducers, one being integral to the plunger, the other being placed at the capillary die entry. The difference in the two pressure readings is the barrel pressure drop, $P_B$. Using this system, the apparent shear viscosity of the material in the barrel, and the viscosity of the material in the capillary (subject to the usual capillary end error correction) can be calculated simultaneously.

Barrel $$q_{a,B} = \left| \frac{\Delta l}{L_B} \right| \times \left| \frac{\pi (R_B)^4}{8Q} \right|$$

where $q_{a_1B}$ = apparent melt shear viscosity in the barrel at $$\gamma_a B = \frac{4Q}{\pi (R_B)^3}$$

apparent shear rate.
Q = volume flow rate, $R_B$ = barrel radius $$\frac{\Delta P}{L_B} = \frac{(\text{Piston} - \text{Pentrance})}{(\text{Effective Barrel Length})}$$

Dynamic but a "constant" at each Q

Capillary $$q_{a,c} = \left| \frac{\Delta P}{L_C} \right| \times \left| \frac{(R_C)^4 \pi}{8Q} \right|$$

$q_{a,c}$ = apparent melt viscosity at $\gamma_{a,c} = \frac{4Q}{\pi (R_C)^3}$ (higher shear rate)

$L_C$ = capillary length
$\Delta P$ = capillary pressure drop

The apparent melt viscosity of the polymer is determined at two shear rates for each polymer speed (melt flow rate) with this system. The melt flow characteristics of the polymer are evaluated over a wider range of shear rates that can be evaluated utilizing a conventional force based capillary rheometer.

Alternate embodiments of capillary rheometer utilizing plunger transducer assemblies are illustrated in FIGS. 5, 6 and 7.

FIG. 5 shows the implementation of a liquid metal filled, rigid stem, capillary rheometer plunger transducer. As can be seen in FIG. 5, the metal case 17, enclosing the measurement diaphragm assembly 15, is attached directly to the plunger 5, rather than from the interim metal armor flex hose 13. This alternate arrangement is thus referred to as a "rigid stem" system.

FIG. 6 shows the implementation of a push rod, rigid stem, Capillary Rheometer plunger transducer. As in FIG. 5, this system is a rigid stem system. The alternate embodiment of FIG. 6 also includes a push rod 27 within the plunger transducer assembly 25. The push rod 27 is indicated predominantly in FIG. 6.

FIG. 7 shows the implementation of a non-bonded piezo resistive type, rigid stem, capillary rheometer plunger transducer. This alternate embodiment, like the embodiments in FIGS. 5 and 6, is a rigid stem system. The alternate embodiment in FIG. 7, however, includes a measurement diaphragm 29 consisting of either a highly elastic non-metallic monocrystalline structure or a polycrystalline structure. Also shown in FIG. 7 are the high-temperature electrical connections 28 for communication with the strand gage 20. Further details of the measurement diaphragm 29 and high-temperature electrical connections 28, which communicate with the strand gage 20, are illustrated in the enlarged, fragmentary, cross-section view of FIG. 7A.

It is to be appreciated that the preferred embodiment of the present invention utilizes a plunger pressure transducer assembly in a force based type capillary rheometer which allows for the determination of melted polymer material properties without certain errors associate with the force based type capillary rheometer, but the plunger pressure transducer assembly is not limited to use in a force based type capillary rheometer.

Having now described a limited number of embodiments of the invention, it should now be apparent to those skilled in the art that numerous embodiments and modifications thereof are contemplated as falling within the scope of the present invention as defined by the appended claims.

What is claimed is:

1. In combination, a heater block holder and a capillary rheometer plunger, said heater block holder removably housing said capillary rheometer plunger, the holder comprising:
   an outer shell having a first aperture defined therein;
   a holder member disposed within said first aperture, said holder member having a second aperture defined therein removably housing said capillary rheometer plunger, the holder member including means for heating the plunger; and
   a base for supporting said shell;
   said capillary rheometer plunger including means defining a liquid-filled capillary passage extending within the plunger.

2. The combination as set forth in claim 1 further including a temperature sensor disposed within said shell for sensing the temperature of said holder, and said heating means comprising a heating element disposed within said shell for heating said holder member substantially to the intended operating temperature of said rheometer plunger being heated.

3. In combination, a heater block holder and a capillary rheometer plunger, the heater block holder removably housing the capillary rheometer plunger, the holder comprising:
   an outer shell having a first aperture defined therein;
   a holder member disposed within the first aperture, the holder member having a second aperture defined therein removably housing the capillary rheometer plunger, the holder member including means for heating the plunger; and
   a base for supporting the shell;
   wherein the capillary rheometer plunger includes a liquid-filled capillary passage extending within the plunger.

* * * * *